United States Patent [19]

Mastel et al.

[11] Patent Number: 4,662,075

[45] Date of Patent: May 5, 1987

[54] APPARATUS AND METHOD FOR SETTING KNIFE BLADE DEPTH

[75] Inventors: Douglas J. Mastel, Magnolia; Alan D. Baribeau, San Antonio, both of Tex.

[73] Assignee: Magnum Diamond Reclamation, Inc., San Antonio, Tex.

[21] Appl. No.: 768,124

[22] Filed: Aug. 22, 1985

[51] Int. Cl.⁴ .............................................. B27G 23/00
[52] U.S. Cl. ......................................... 33/628; 33/201
[58] Field of Search ...................... 33/185 R, 201, 170, 33/169 R, 169 B, 125 A; 356/399, 401, 372, 375, 392, 393

[56] References Cited

U.S. PATENT DOCUMENTS

| | | | |
|---|---|---|---|
| 1,761,260 | 6/1930 | Gallash | 356/372 |
| 3,167,868 | 2/1965 | Arneson | 33/185 R |
| 4,329,785 | 5/1982 | Peterson | 33/185 R |
| 4,495,701 | 1/1985 | Nakadoi | 33/170 |
| 4,538,356 | 9/1985 | Knepshield et al. | 33/185 R |

Primary Examiner—Charles Frankfort
Assistant Examiner—Patrick Scanlon
Attorney, Agent, or Firm—Gunn, Lee & Jackson

[57] ABSTRACT

Apparatus and method for setting knife blade depth. The apparatus comprises a magnification device and a removable tray in operative engagement with a digital micrometer. The method comprises the steps of positioning the edge of the knife holder flush with a fixed vertical plane extending through a reticle axis within the magnification device, zeroing the micrometer, rotating the micrometer handle until the tray and edge of the knife holder have moved a predetermined distance away from the fixed plane, and adjusting the knife blade until the edge of the knife blade is flush with the fixed plane.

16 Claims, 12 Drawing Figures

APPARATUS AND METHOD FOR SETTING KNIFE BLADE DEPTH

BACKGROUND OF THE INVENTION

The present invention relates to an apparatus and method for setting knife blade depth for microsurgical applications.

Various types of knives have heretofore been utilized in microsurgical applications, such as the surgical technique known as radial keratotomy. For example, a steel blade fragment is placed between the jaws of a holder and the blade depth is thereafter set with a sight gauge under microscopic observation. Although the steel blade is generally considered the sharpest blade, it has a tendency to tear on a cellular level during use in microsurgical applications. For this reason, a diamond or sapphire blade knife, which uses a micrometer to control the exposure of the blade in discreet increments, has become increasingly popular for use in microsurgical applications. Regardless of the type of knife utilized, however, the setting of the knife blade depth requires accurate measurement of the length of extension of the blade edge relative to the edge or feet of the blade holder.

In a micrometer knife, the micrometer handle is in operative engagement with either the blade or the feet of the knife. The blade depth, or length of extension of the blade relative to the feet of the knife, is set by rotating the micrometer handle. However, play in the micrometer frequently results in an undesirable deviation from the desired knife blade depth. A sight gauge has also been used to check the knife blade depth of a knife set by means of a micrometer handle.

Figures 1, 1A:
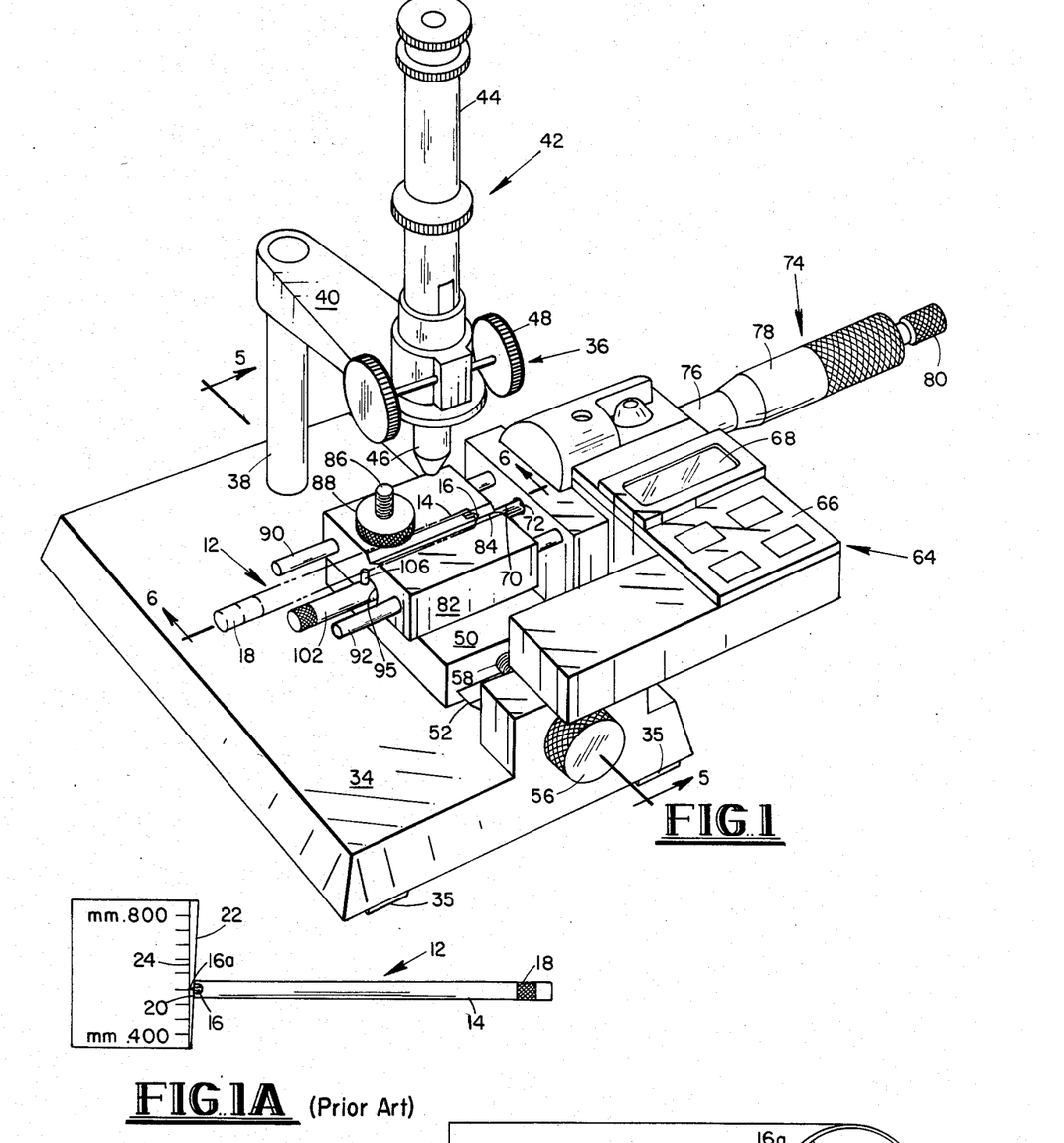
FIG. 1 is a perspective view of a preferred embodiment of an apparatus and method for setting knife blade depth.
FIGS. 1A-1B illustrate previous methods and apparatus for setting knife blade depth.
Figure 1B:
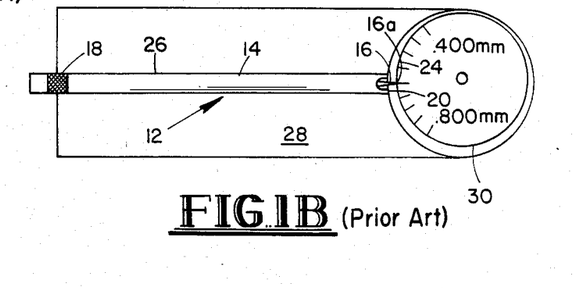

The setting of knife blade depth has heretofore also involved the utilization of a sight gauge, such as the block gauge illustrated in FIG. 1A or the coin gauge illustrated in FIG. 1B. The sight gauges illustrated in FIGS. 1A and 1B are shown measuring the blade depth of a conventional diamond blade knife 12 comprising a blade holder 14 and a diamond tipped blade 16 having an outer edge 16a. The blade holder 14 has a micrometer handle 18 on one end thereof in operative engagement with the diamond tipped blade 16. Rotation of the micrometer 18 causes the blade 16 to move inward or outward from the base or feet 20 of the blade holder 14 on the opposite end of the knife 12 from micrometer 18. Once again, however, conventional knives have also been utilized wherein the blade is fixed and the micrometer is in operative engagement with the feet.

As illustrated in FIG. 1A, the block gauge consists of a substantially planar material having a tapered surface 22 on one edge thereof and a plurality of perpendicular gradient marks 24 corresponding to the degree of taper. Usage of the block gauge illustrated in FIG. 1A entails the placement of the feet 20 flush against the tapered edge 22 and reading of the corresponding gradient mark intersecting the tip or edge 16a of blade 16. If the tip or edge 16a of the blade 16 does not extend the desired distance outward from the feet 20, the handle of micrometer 18 is rotated until the edge 16a of blade 16 intersects the desired gradient mark reflecting the degree of extension.

Usage of a coin type sight gauge, as illustrated in FIG. 1B, entails the placement of the knife 12 within the groove 26 of a tray 28. An eccentrically machined lip 30 having gradient marks 24 is thereafter rotated until the edge or tip 16a of the knife 16 intersects the lip 30. The point at which the edge or tip 16a of the blade 16 intersects the lip 30 reflects the degree of extension of the blade 16 outward from the blade holder 14. Once again, however, blade 16 can be adjusted by means of micrometer 18 until edge 16a extends the desired distance outward from feet 20, as measured by the gauge. In an effort to increase the accuracy of blade depth settings, the measurement of the blade depth of a micrometer knife with a sight gauge has heretofore also been done under microscopic observation.

Figure 1C:
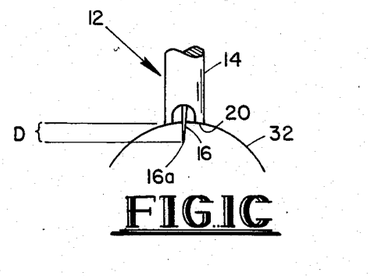
FIG. 1C illustrates surgical use of a knife having a blade movable relative to a blade holder.

Regardless of the type of knife utilized in the microsurgical application, it is extremely important that the knife blade depth, or length of extension of the blade edge 16a relative to the feet or edge 20 of the blade holder 14, be set with precision. For example, in radial keratotomy surgery, a number of radial incisions are made in the cornea by placing the feet or edge 20 of the knife holder 14 against the periphery of the cornea. In order to achieve the desired predetermined incision depth, the knife blade depth must be accurately set so that the edge 16a of the blade 16 only protrudes outward from the blade holder 14 by a distance equivalent to the desired incision depth. That is, in radial keratotomy surgery, the knife 12 is placed in proximity to the patient's eye until the feet 20 rest atop the cornea 32, as illustrated in FIG. 1C. The blade 16 thereby cuts the cornea 32 to a depth D equivalent to the distance between the tip or edge 16a of the blade 16 and the edge or feet 20 of the blade holder 14. In a typical radial keratotomy surgery, the cornea has a depth of approximately 0.6 millimeters (mm) and the radial incision cuts through approximately ninety percent (90%) of the cornea, or to approximately a depth of 0.54 mm. The surgical knife must therefore be accurately set so that the edge 16a of the blade extends outward away from the edge 20 of the blade holder 14 precisely 0.54 mm. A deviation of any magnitude could result in dangerous perforations of the cornea and/or damage to the patient's vision.

Despite the importance of accurately setting the knife blade depth, play in the micrometer handle has resulted in undesirable deviation from the desired knife blade depth and the sight gauges which have heretofore been utilized have been found to be inherently unreliable. For example, the use of a sight gauge, such as the block gauge and coin gauge illustrated in FIG. 1A and FIG. 1B, respectively, may result in parallax error, perhaps as high as ten percent (10%). Such error occurs in reading the gauge due to the fact that the observer's eye and the edge or tip 16a of the blade 16 are not in a line perpendicular to the plane of the scale. Further, repeated contact of the blade 16 with the gauge may result in degradation and damage to the blade 16. Finally, degradation of the gauge materials may result in a gradient variability as high as thirty percent (30%).

SUMMARY OF THE INVENTION

Accordingly, the present invention provides an apparatus and method for setting the length of extension of a blade edge relative to an edge of the blade holder, which effectively eliminates the limitations and inaccuracies inherent in prior devices and methods for setting blade depth, such as the micrometer knives and sight gauges discussed hereinabove. The present invention eliminates parallax errors as well as the necessity of contacting the edge of the blade with a gradient surface. Further, setting knife blade depth without the use of a gradient surface eliminates any possible inaccuracy due to degradation of gradient surface materials.

The apparatus of the present invention comprises a base having a microscope and a movable table mounted thereon. A removable tray having a groove therein for receiving a knife thereon is connected to the table beneath the microscope. A digital micrometer having a spindle which abuts against a side of the tray in operative engagement therewith is also connected to the table. The microscope lens has a reticle axis through which a fixed vertical plane extends.

The apparatus of the present invention may also be designed to facilitate the setting of the knife blade depth of a knife wherein the feet are movable relative to the blade which functions as the baseline reference. For purposes of clarity, however, the present apparatus and method will be described with reference to the setting of the blade depth of a knife having a blade movable relative to a blade holder, such as by means of a micrometer handle in operative engagement with the blade. In such a knife, the feet or edge of the blade holder function as the baseline reference.

The method for setting the blade depth of a knife having a blade movable relative to a blade holder comprises the steps of placing the knife on the tray whereby the feet or edge of the blade holder intersects the referenced fixed plane. This is accomplished by moving the tray and focusing the microscope on the edge of the blade holder until the holder edge appears flush with the reticle axis. The digital micrometer is thereafter zeroed and the digital micrometer handle rotated until the digital micrometer reading is equivalent to the desired length of extension of the knife blade. Rotation of the digital micrometer handle causes the digital micrometer spindle to move the tray and knife holder a distance away from the fixed plane substantially equivalent to the distance reflected on the digital micrometer reading. The microscope is thereafter focused on the blade and the micrometer in the knife handle is rotated until the edge or tip of the blade appears flush with the reticle axis.

The present invention is also designed to permit the tray to be readily removed from the table for sterilization or cleaning purposes. Further, the apparatus is preferably provided with a light source perpendicular to the edge of the blade holder to facilitate identification of the edge of the holder and knife edge. Finally, the digital micrometer may be provided with a computer innerface in order to document the blade settings with a tape or printout.

DETAILED DESCRIPTION OF THE PREFERRED EMBODIMENT

The preferred embodiment of an apparatus and method for setting knife blade depth is illustrated in FIG. 1. The apparatus comprises a base 34 which may be provided with a plurality of pads 35. A microscope 36 is connected to the base 34 by means of a post 38 and arm 40. The lowermost end of post 38 is connected to base 34 in a conventional manner, such as by means of the threaded engagement illustrated in FIG. 5. The uppermost end of post 38 is also connected to the arm 40 in a conventional manner. The microscope 36 further comprises a body tube 42 which has an eye piece 44 and an objective 46. Body tube 42 is connected to arm 40 in a conventional manner. The body tube 42 may be adjusted vertically relative to base 34, and microscope 36 may be focused, by rotating a pair of focus control knobs 48. The microscope 36 preferably has a lens with a calibrated reticle thereon. Microscope 36 is preferably a conventional microscope having a magnification of 100 power (100×) or greater.

Figure 4:
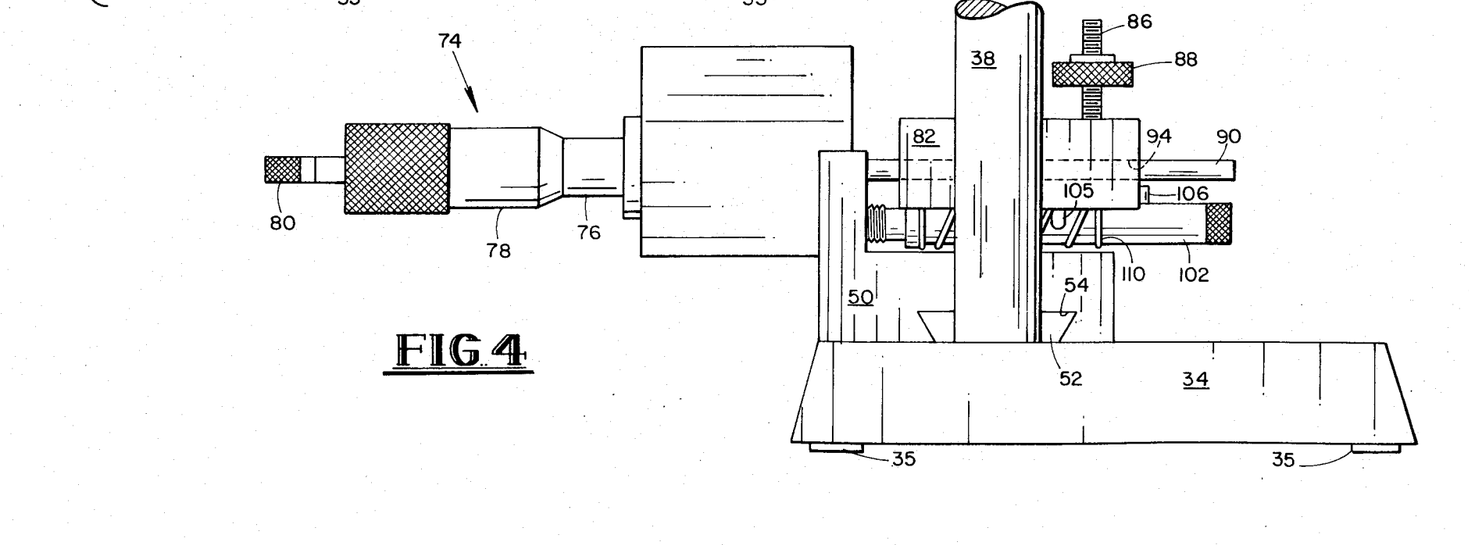
FIG. 4 is a partial, rear view of a preferred embodiment of an apparatus and method for setting knife blade depth.
Figure 5:
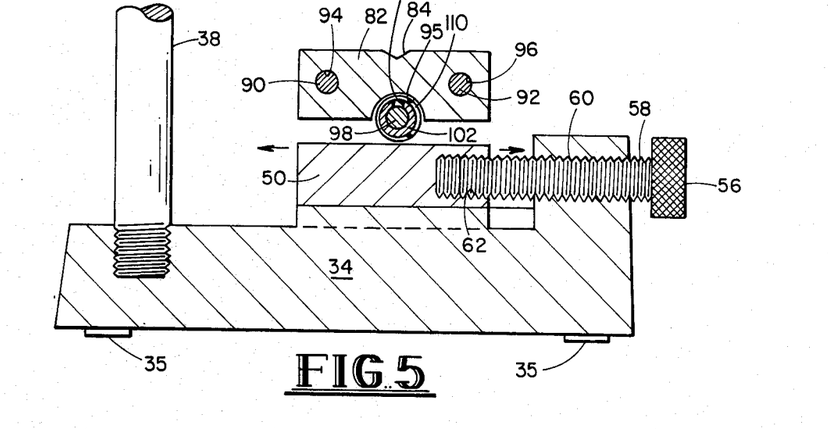
FIG. 5 is a partial cross-sectional view taken along section lines 5—5 of FIG. 1 illustrating movement of the table in a preferred embodiment of an apparatus and method for setting knife blade depth.

Referring again to FIG. 1, a movable table 50 is preferably mounted atop base 34 in sliding engagement with a dovetail shaped wedge 52 which is connected to base 34. As illustrated in FIG. 4, wedge 52 extends into a similarly shaped passage 54 in table 50. As illustrated in FIG. 1 and FIG. 5, a table adjustment knob 56 having a threaded bolt 58 connected thereto extends through a threaded passage 60 in base 34 and a threaded passage 62 in table 50 in threaded engagement with base 34 and table 50. Due to the threaded engagement of bolt 58 within passage 62, rotation of knob 56 in the desired direction causes table 50 to move in the desired direction atop base 34, as illustrated by the shaded arrows in FIG. 5. That is, rotation of knob 56 in a first direction will cause table 50 to move atop base 34 toward post 38. Rotation of knob 56 in a second direction, opposite the first direction, will cause table 50 to move atop base 34 toward knob 56. The apparatus may also be provided with a set screw (not shown) through base 34 into bolt 58 to lock out any undesired movement of table 50.

Referring again to FIG. 1, the preferred embodiment of an apparatus for setting knife blade depth further comprises a digital micrometer 64 which is bolted or otherwise appropriately connected to the table 50. The micrometer 64 can be a type such as Mitutoyo Model No. 293-301 which is adapted as necessary, such as by removal of the anvil, to fit the structure of the embodiment disclosed herein. The micrometer 64 comprises an input/output board 66 and a display 68. The micrometer 64 further comprises a spindle 70 which extends through a passage 72 in table 50. The spindle 70 is activated by micrometer handle 74 comprising a sleeve 76, a thimble 78, and a screw 80.

Again referring to FIG. 1, the preferred embodiment of an apparatus for setting knife blade depth further comprises a stainless steel tray or stage 82 having a central groove 84 on the top thereof extending the length of the tray 82 and an undercut 95 on the bottom thereof, also extending the length of the tray 82. As further illustrated in FIG. 1, groove 84 is adapted to receive a conventional knife 12 comprising a blade holder 14 and a blade 16 movable relative to the blade holder 14 by means of a micrometer handle 18 in operative engagement with blade 16. The tray 82 is additionally provided with a knife locking mechanism comprising a bolt 86 in threaded engagement with tray 82 and a brass locking knob 88. Knob 88 abuts against blade holder 14 to maintain the position of knife 12 within tray 82.

Figure 2:
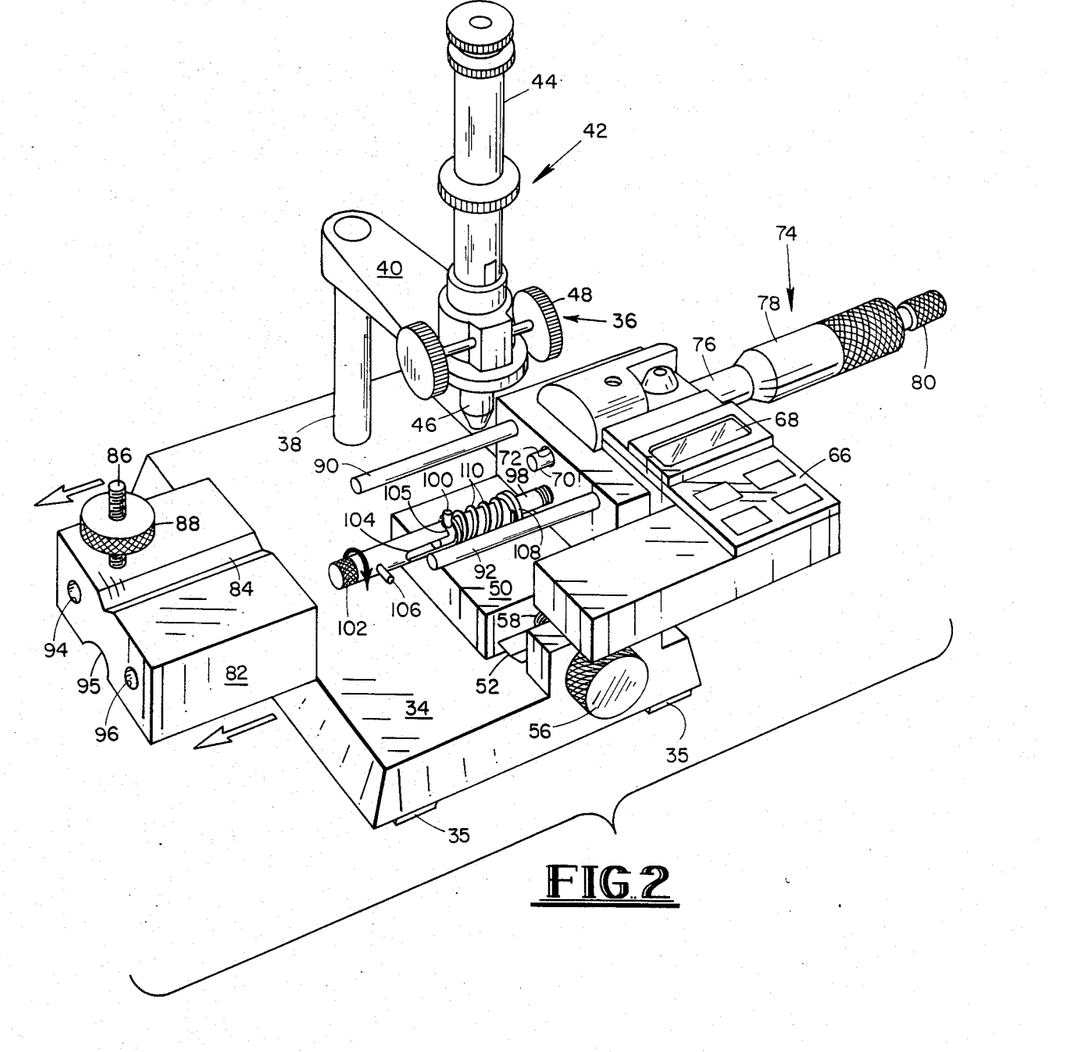
FIG. 2 is a perspective view of a preferred embodiment of an apparatus and method for setting knife blade depth illustrating removal of the knife tray.

Referring to FIG. 1 and FIG. 2, the removable attachment of tray 82 to table 50 is facilitated by a pair of table dowels 90 and 92 which are appropriately connected to table 50 and normally extend through passages 94 and 96, respectively, in tray 82. A rod 98 is also in threaded engagement with table 50 and has an upstanding pin 100 connected thereto, as illustrated in FIG. 2. As further illustrated in FIG. 2, a rotatable sleeve 102 has a groove 104 and a notch 105 therein to permit extension of pin 100 therethrough and sliding engagement of sleeve 102 on rod 98. Notch 105 is substantially perpendicular to groove 104. Sleeve 102 has a pin 106 on one end thereof and an annular lip 108 on the opposite end thereof. A tension spring 110 is positioned about sleeve 102 intermediate pin 100 and lip 108. The groove 84 facilitates alignment of the knife 12 and the undercut 95 permits ready passage of the tray 82 over the sleeve 102.

Figure 6:
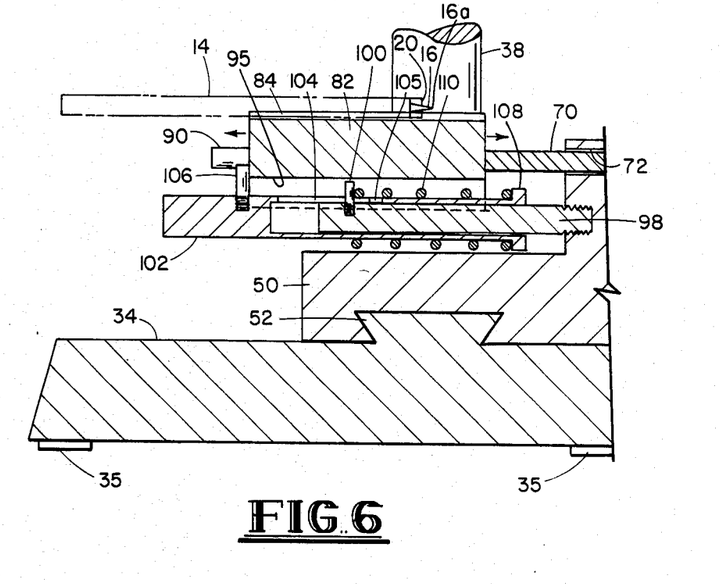
FIG. 6 is a cross-sectional view taken along section lines 6—6 of FIG. 1 illustrating movement of the tray in a preferred embodiment of an apparatus and method for setting knife blade depth.

The tray 82 is slidable along dowels 90 and 92 and normally abuts against or is held in flush engagement with spindle 70 by means of pin 106, as illustrated in FIG. 1 and FIG. 6. Pin 106 is normally biased toward spindle 70 due to the outward tension or expansion of spring 110 between lip 108 and pin 100. However, as illustrated in FIG. 2, the tray 82 can be readily removed from dowels 90 and 92 by urging sleeve 102 and pin 106 in the direction illustrated by the clear arrows. When sleeve 102 and pin 106 are fully extended, the sleeve 102 and pin 106 may be rotated, as illustrated by the shaded arrow in FIG. 2. Such rotation causes the pin 100 to be received by notch 105. The sleeve 102 and pin 106 are thereby placed in the open, locked position to permit the ready removal of tray 82 from dowels 90 and 92. That is, in the open, locked position illustrated in FIG. 2, pin 106 no longer abuts against tray 82. Tray 82 can thereafter be removed from dowels 90 and 92 by sliding tray 82 in the direction of the clear arrows illustrated in FIG. 2.

Figure 3:
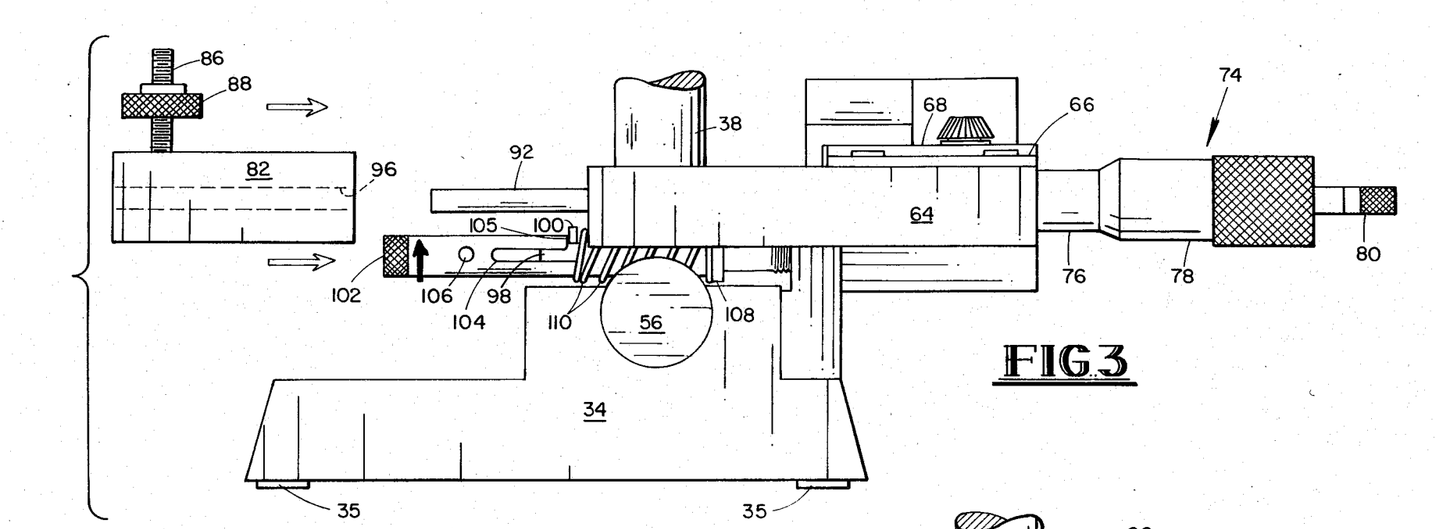
FIG. 3 is a partial, front view of a preferred embodiment of an apparatus and method for setting knife blade depth illustrating replacement of the removable tray.

The removable tray 82 may again be placed in operative engagement with spindle 70 by reinserting dowels 90 and 92 through passages 94 and 96, respectively, as illustrated by the clear arrows in FIG. 3, when sleeve 102 and pin 106 are in the open, locked position. Sleeve 102 and pin 106 are thereafter rotated in the opposite direction, illustrated by the shaded arrow in FIG. 3, thereby removing pin 100 from notch 105. The tension of spring 110 between lip 108 and pin 100 thereafter urges pin 106 toward spindle 70. Pin 106 thereafter abuts against tray 82, as illustrated in FIG. 4 and FIG. 6, until it is again desired to remove tray 82.

The method for setting a knife blade 16 which is movable relative to a blade holder 14 comprises the following steps. The tray 82 is initially sterilized and the knife 12 or blade holder 14 is placed within the groove 84, as illustrated in FIG. 1. The knife 12 is thereafter locked in place by rotating locking knob 88 until knob 88 impinges against blade holder 14. It is to be understood that the tray 82 may be readily removed, as described hereinabove, for cleaning or sterilization purposes and that the knife 12 may be locked securely atop tray 82 before or after the tray 82 is placed in operative engagement with spindle 70.

Figure 7:
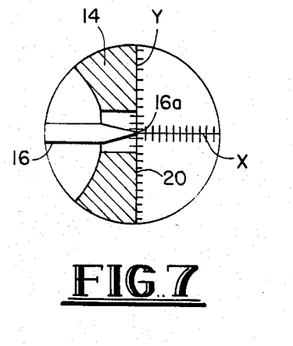
FIG. 7–FIG. 9 are sequential views through a microscope lens illustrating steps in a preferred method for setting knife blade depth.

Once the knife 12 is mounted atop tray 82 and the tray 82 is mounted to table 50 on dowels 90 and 92, as described hereinabove, the table 50 and tray 82 are adjusted and the microscope 36 is focused until the feet or edge 20 of blade holder 14 appear flush with the Y axis of the lens reticle, as illustrated in FIG. 7. As illustrated in FIG. 5 and described hereinabove, the table 50 is adjusted in either direction indicated by the shaded arrows by rotating table adjustment knob 56 in the appropriate direction. As illustrated in FIG. 6, the tray 82 is adjusted in either direction indicated by the shaded arrows by rotating micrometer handle 74. That is, rotation of micrometer handle 74 in a first direction causes spindle 70 to urge tray 82 away from micrometer handle 74. Rotation of micrometer handle 74 in a second direction, opposite the first direction, releases the tension of spindle 70 against tray 82 and allows pin 106 to urge tray 82 toward micrometer handle 74. Finally, as illustrated in FIG. 1, the microscope 36 may be focused upon feet 20 by means of focus control knobs 48.

Figure 8:
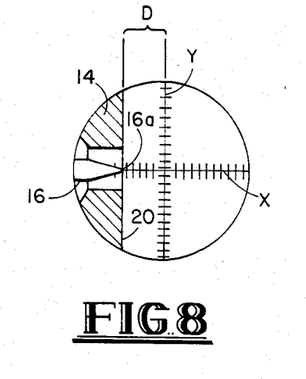
Figure 9:
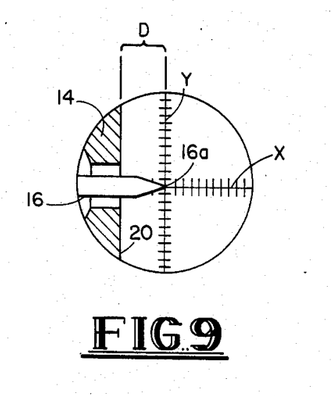

Once the feet 20 appear flush against the Y axis, as illustrated in FIG. 7, and spindle 70 is flush against the side of table 82, as illustrated in FIG. 6, the digital micrometer 64 is zeroed by pressing the appropriate key on the input/output board 66. The feet 20 are thereby flush with a fixed vertical plane which extends through the Y axis. The micrometer handle 74 is thereafter rotated until the display 68 reflects the predetermined desired length of extension of the blade 16 outward from the blade holder 14 based upon the desired incision depth. Rotation of micrometer handle 74 causes spindle 70 to urge or move tray 82 along dowels 90 and 92, and thereby move feet 20 away from the fixed plane extending through the lens reticle Y axis, as illustrated in FIG. 8. The spindle 70 thereby moves the tray 82 and feet 20 a distance or length D away from the fixed vertical plane extending through the reticle Y axis. The microscope 36 is thereafter focused on blade 16 by knobs 48 and the micrometer 18 on the opposite end of knife 12 is rotated until the tip or edge 16a of blade 16 appears flush with the reticle Y axis, as illustrated in FIG. 9. At this point in time, the edge 16a of blade 16 extends outward from the edge 20 of blade holder 14 by a distance D and intersects the fixed vertical plane extending through the reticle Y axis.

Once the blade tip 16a appears flush with the Y axis, as illustrated in FIG. 9, the knife 12 may be removed from the tray 82 by rotating knob 88 until knob 88 no longer impinges against blade holder 14. The knife 12 may thereafter be utilized for surgical applications such as radial keratotomy, as described hereinabove and illustrated in FIG. 1C, and another knife may be set using the above described apparatus and method. It is to be understood that the depth of incision D, as illustrated in FIG. 1C, will be equivalent to the length of extension D of blade tip 16a relative to feet 20, as illustrated in FIG. 9, which will also be equivalent to the predetermined length or depth of extension reflected in the display 68.

The present invention is able to substantially eliminate parallax errors due to the fact that both the feet 20 and blade edge 16a are adjusted relative to the same fixed plane or reference. Further, utilization of the present invention eliminates any contact between the blade 16 and a gradiant surface. Finally, the present invention is able to achieve approximately one thousand percent greater knife depth accuracy than the prior art methods and devices.

It is to be understood that the measuring reticle within the lens of microscope 36 is preferably a calibrated cross hair reticle, such as a photo S reticle, which may function as a safety check against the digital micrometer 64. It is also to be understood that the appearance of the blade holder 14 and blade 16 through the microscope lens may be a reverse image or optically inverted. Further, a certified gauge block may be placed atop tray 82 and utilized to check the accuracy of the apparatus. It is also to be understood that the apparatus of the present invention is preferably provided with a light source (not shown) perpendicular to the edge 20 of the blade holder 14 to facilitate identification of the edge 20 of the holder 14 and knife edge 16a. The apparatus may also be provided with a light source (not shown) behind the knife 12 to enable inspection of the blade 16 for defects. The digital micrometer microprocessor base unit 64 may also be provided with a hard copy interface (not shown) in order to document the blade settings with a tape or printout.

It is also to be understood that the present invention can be designed and used for knives wherein the knife blade is fixed to the blade holder and the knife micrometer or blade holder adjusts the position of the feet, i.e., wherein the edge of the blade is the baseline reference. In such a design, the micrometer spindle 70 impinges against the opposite side of the tray 82 and the tray 82 moves in the opposite direction relative to the fixed plane. That is, the edge or tip of the blade initially intersects the fixed vertical plane which extends through the Y axis and the digital micrometer 64 is zeroed. The digital micrometer handle 74 is thereafter rotated until the fixed blade has moved the desired distance across the Y axis along the X axis. The feet of the knife are thereafter adjusted by the blade holder or knife micrometer until the feet are flush with the fixed plane.

It is also to be understood that the present invention may be utilized to measure or check the preset blade depth of a knife, such as a disposable knife, wherein neither the blade nor feet are movable relative to the other. The feet of the knife are initially placed flush with the fixed vertical plane which extends through the Y axis and the digital micrometer 64 is zeroed with spindle 70 flush against the side of tray 82. The digital micrometer handle 74 is thereafter rotated until the edge of the blade appears to intersect the Y axis flush with the fixed plane. The reading on the display 68 will thereafter reflect the actual extension of the edge of the blade outward from the feet. It is also to be understood that the present invention may be utilized to inspect for defects or deviations in the feet or knife blade. It is also to be understood that knobs 48, 56, and/or 88 may be provided with sterilizable sleeves.

While the apparatus and method for setting knife blade depth has been described in connection with the preferred embodiment, it is not intended to limit the invention to the particular form set forth, but on the contrary, it is intended to cover such alternatives, modifications, and equivalents, as may be included within the spirit and scope of the invention as defined by the appended claims.

We claim:

1. Apparatus for setting a knife blade which is movable relative to a blade holder and which has an outermost edge or tip, said apparatus setting the length of extension of said outermost edge or tip of said blade relative to an edge of said blade holder, comprising:
   a tray for receiving said blade holder fixedly thereon, said tray with said blade holder fixedly attached being movable with respect to a fixed plane, said outermost edge or tip of said blade aligned with said fixed plane; and
   means in operative engagement with said tray for moving said tray with said blade holder fixedly thereon a predetermined distance relative to sasid fixed plane, thereby moving said outermost edge of said blade holder said predetermined distance away from said fixed plane, said outermost edge of said blade thereafter being moved with respect to said blade holder by adjustment means until said outermost edge aligns with said fixed plane, said length of extension of said outermost edge moved by said adjustment means thereby being equivalent to said predetermined distance.

2. Apparatus for setting a knife blade wherein an edge of a holder of said blade is movable relative to said blade and said blade has an outermost edge or tip, said apparatus setting the length of extension of said outermost edge or tip of said blade relative to said edge of said blade holder, comprising:
   a tray for receiving said blade holder fixedly thereon, said tray, with said blade holder fixedly attached, being movable with respect to a fixed plane, said outermost edge or tip of said blade aligned with said fixed plane; and
   means in operative engagement with said tray for moving said tray with said blade holder fixedly attached thereon a predetermined distance relative to said fixed plane, thereby moving said outermost edge or tip of said blade said predetermined distance away from said fixed plane, said outermost edge of said blade holder thereafter being moved with respect to said blade by adjustment means until said blade holder edge aligns with said fixed plane, said length of extension of said outermost edge or tip thereby being equivalent to said predetermined distance.

3. Apparatus for setting a knife blade, as recited in claim 1 or 2, further comprising means for magnifying said outermost edge or tip of said blade and said edge of said blade holder.

4. Apparatus for setting a knife blade, as recited in claim 1 or 2, wherein said tray has a groove therein for receiving said blade holder.

5. Apparatus for setting a knife blade, as recited in claim 3, wherein said magnifying means includes a reticle and said fixed plane is a verticle plane which extends through an axis of said reticle.

6. Apparatus for setting a knife blade, as recited in claim 1 or 2, wherein said apparatus further comprises means for securing said blade holder to said tray.

7. Apparatus for setting a knife blade, as recited in claim 1 or 2, further comprising means for alternately engaging or disengaging said tray with or from said tray moving means.

8. Apparatus for setting a knife blade, as recited in claim 1 or 2, wherein said tray moving means comprises a digital micrometer having a spindle for engaging said tray.

9. A method for setting a knife blade which is movable relative to a blade holder, said method setting the length of extension of an outermost edge or tip of said blade away from an edge of said blade holder, comprising the steps of:
(a) positioning said blade holder on a tray whereby said edge of said holder is aligned with a fixed plane;
(b) moving said tray a predetermined distance relative to said fixed plane, thereby moving said edge of aid blade holder away from said fixed plane by said predetermined distance; and
(c) moving said outermost edge or tip of said blade relative to said blade holder until said outermost edge or tip of said blade aligns with said fixed plane, said outermost edge or tip extending thereby a distance equivalent to said predetermined distance.

10. A method for setting a knife blade which is movable relative to a blade holder, said method setting the length of extension of an outermost edge or tip of said blade away from an edge of said blade holder, comprising the steps of:
(a) engaging a tray with a digital micrometer adpated for moving said tray a predetermined distance;
(b) positioning said blade holder on said tray whereby said edge of said holder is aligned with a fixed vertical plane;
(c) focusing a magnifying means on said edge of said holder, said magnifying means including a reticle having an axis through which said fixed vertical plane extends;
(d) moving said tray said predetermined distance relative to said fixed plane, thereby moving said edge of said holder away from said fixed vertical plane by said predetermined distance;
(e) focusing said magnifying means on said outermost edge or tip of said blade; and
(f) moving said outermost edge or tip of said blade relative to said blade holder until said outermost edge or tip of said blade is aligned with said fixed vertical plane, said outermost edge or tip extending thereby a distance equivalent to said predetermined distance.

11. A method for setting a knife blade, as recited in claim 10, further comprising the step of sterilizing said tray prior to engaging said tray with said digital micrometer.

12. A method for setting a knife blade, as recited in claim 10, wherein said step of moving said tray comprises the steps of zeroing said micrometer and rotating a handle of said micrometer, said handle causing a spindle of said micrometer, engaged with said tray, to move said tray said predetermined distance.

13. A method for setting a knife blade, as recited in claim 10, further comprising the step of removing said blade holder from said tray.

14. A method for setting a knife blade, wherein an edge of a holder of said blade is movable relative to said blade, said method setting the length of extension of an outermost edge or tip of said blade away from said edge of said blade holder, comprising the steps of:

(a) positioning said blade holder on a tray whereby said outermost edge or tip of said blade is aligned with a fixed plane;
(b) moving said tray a predetermined distance relative to said fixed plane, thereby moving said outermost edge or tip of said blade away from said fixed plane by said predetermined distance; and
(c) moving said blade holder edge relative to said blade until said blade holder edge is aligned with said fixed plane, said outermost edge or tip extending thereby a distance equivalent to asid predetermined distance.

15. A method for measuring the length of extension of an outermost edge or tip of a blade away from an edge of a blade holder, comprising the steps of:
(a) engaging a tray with a digital micrometer adapted for moving said tray relative to fixed plane;
(b) positioning said blade holder on said tray whereby said outermost edge or tip of said holder is aligned with said fixed plane;
(c) focusing a magnfiying means on said edge of said holder, said magnifying means including a reticle having an axis through which said fixed plane extends;
(d) moving said tray relative to said fixed plane until said outermost edge or tip of said blade is aligned with said fixed plane; and
(e) reading the measurmenet reflected on a display of said digital micrometer.

16. Apparatus for setting a knife blade which is movable relative to a blade holder and which has an outermost edge or tip, said apparatus setting the length of extension of said outermost edge or tip of said blade relative to an edge of said blade holder, comprising:
a base;
a table connected to said base;
a tray removably connected to said table for receiving said blade holder thereon, means in operative engagement with said tray for moving said tray with respect to a fixed plane said outermost edge or tip of said blade aligned with said fixed plane;
means connected to said tray for securing said blade holder fixedly to said tray;
means mounted to said base for magnifying said outermost edge or tip of said blade and for magnifying said blade holder;
a digital micrometer connected to said table having a spindle in operative engagment with said tray for moving said tray with said blade holder fixedly attached thereon a predetermined distance relative to said fixed plane, thereby moving said edge of said blade holder said predetermined distance away from said fixed plane said outermost edge or tip of said blade thereafter being moved with respect to said blade holder by adjustment means until said blade edge aligns with said fixed plane, said length of extension of said outermost edge or tip thereby being equivalent to said predetermined distance; and
means for maintaining said spindle in operative engagement with said tray comprising a rod connected to said table, a sleeve about said rod having a sleeve pin extending outward therefrom and a lip, said sleeve pin abutting a side of said tray, and a spring about said sleeve intermediate said lip and a rod pin extending outward from said rod.

* * * * *